United States Patent [19]

Mors

[11] Patent Number: 5,618,174

[45] Date of Patent: Apr. 8, 1997

[54] ORTHODONTIC BRACKET AND SYSTEM

[76] Inventor: Wayne A. Mors, 715 W. Judd St., Woodstock, Ill. 60098

[21] Appl. No.: 242,729

[22] Filed: May 11, 1994

[51] Int. Cl.⁶ .................................................. A61C 3/00
[52] U.S. Cl. ................................................. 433/8; 433/10
[58] Field of Search ........................... 433/8, 9, 10, 11, 433/12, 13, 14, 15, 16, 17

[56] References Cited

U.S. PATENT DOCUMENTS

| | | |
|---|---|---|
| 1,976,141 | 10/1934 | Richardson . |
| 2,908,974 | 10/1959 | Stifter .......................................... 433/16 |
| 3,421,221 | 1/1969 | Silverman et al. ........................... 433/8 |
| 3,423,833 | 1/1969 | Pearlman .................................. 433/8 X |
| 3,922,787 | 12/1975 | Fischer et al. ........................... 433/8 X |
| 4,216,583 | 8/1980 | Reynolds . |
| 4,249,897 | 2/1981 | Anderson . |
| 4,322,206 | 3/1982 | Reynolds . |
| 4,337,037 | 6/1982 | Kurz . |
| 4,340,363 | 7/1982 | Klein et al. . |
| 4,373,914 | 2/1983 | Colbert . |
| 4,531,911 | 7/1985 | Creekmore . |
| 4,669,980 | 6/1987 | Degnan . |
| 4,674,978 | 6/1987 | Acevedo ...................................... 433/8 |
| 4,797,095 | 1/1989 | Armstrong et al. . |
| 4,826,430 | 5/1989 | Chen et al. . |
| 4,842,513 | 6/1989 | Haarmann . |
| 4,850,865 | 7/1989 | Napolitano ................................. 433/8 |
| 4,878,840 | 11/1989 | Reynolds . |
| 4,902,224 | 2/1990 | Collins et al. . |
| 4,917,602 | 4/1990 | Broussard . |
| 4,927,360 | 5/1990 | Pospisil . |
| 4,954,080 | 9/1990 | Kelly et al. . |
| 5,044,946 | 9/1991 | Cleary . |
| 5,062,794 | 11/1991 | Miura ....................................... 433/8 X |
| 5,078,596 | 1/1992 | Carberry et al. . |
| 5,269,681 | 12/1993 | Degnan ..................................... 433/11 |

OTHER PUBLICATIONS

Rocky Mountain Orthodontics catalog excerpts, copyright 1992 RMO, Inc.
3M Unitek catalog excerpts (1993).
Class One® Orthodontics catalog excerpts and Price List (1993).
Dentaurum, Inc., Orthodontic Products Catalog and Price List (1993).
American Orthodontics catalog excerpts and Price List (1993).
Orec® Corporation literature, "Ordering the Basics is Basic" (1993).
Ortho Organizers, Inc. Catalog and Ordering Information (excerpts) (1993).
"A"–Company catalog excerpts, copyright 1993.
Ormco® Corporation catalog excerpts, copyright 1992.
3M Unitek literature, "3M Unitek Miniature Twin Bracket System," printed 0691.

*Primary Examiner*—Nicholas D. Lucchesi
*Attorney, Agent, or Firm*—Dressler, Goldsmith, Milnamow & Katz, Ltd.

[57] ABSTRACT

A miniature orthodontic bracket having a slender aspect ratio and small base area. The bracket may be partially tapered in the occlusal half, with sides joining at a point and forming an acute angle. A deflecting tip may be provided on an occlusal extension of the base, and the archwire slot may be located in the gingival one half.

60 Claims, 4 Drawing Sheets

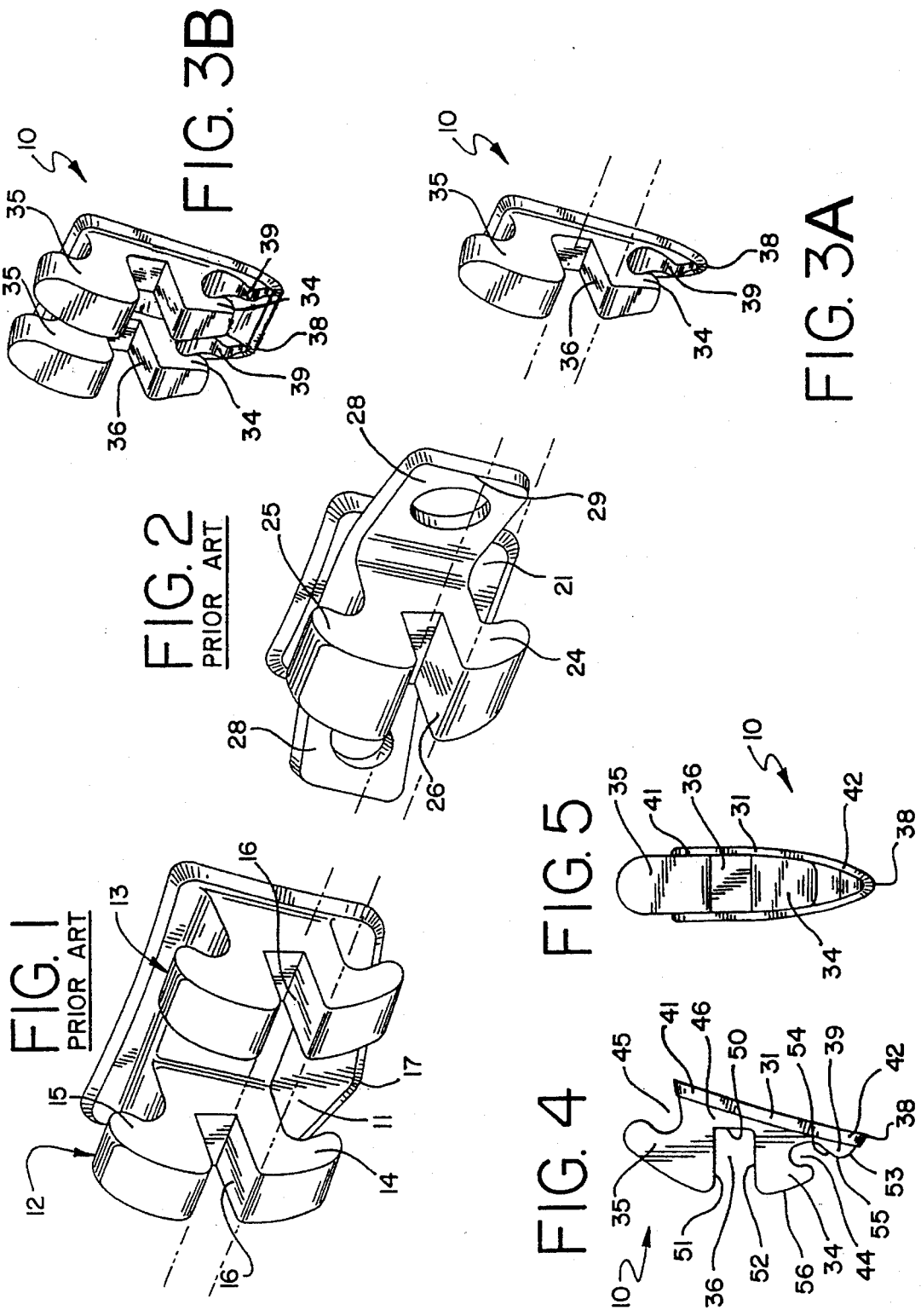

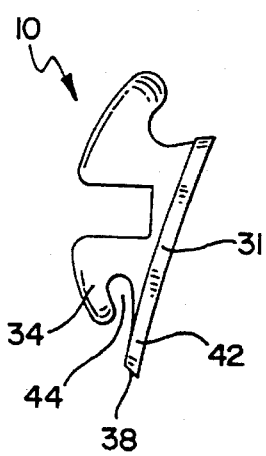
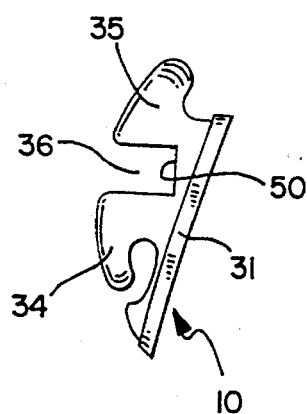
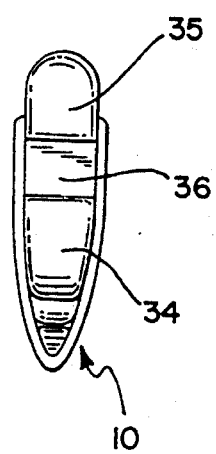
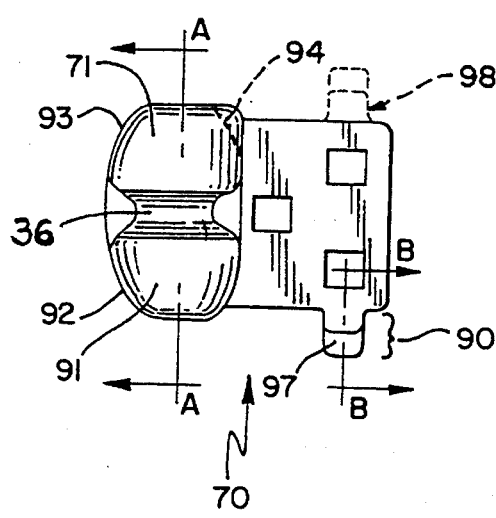
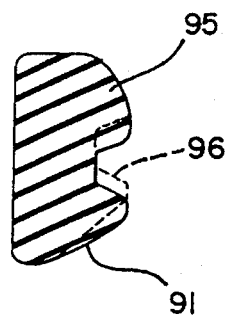
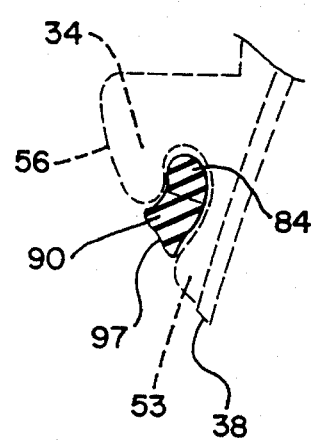

ns,174

ORTHODONTIC BRACKET AND SYSTEM

TECHNICAL FIELD

This invention relates generally to orthodontic appliances and an orthodontic system, and more specifically to a miniature bracket adapted for use with an archwire and including design features to minimize dislodging occlusal forces, a rotation wedge for use with a single bracket, and an orthodontic system including both.

BACKGROUND OF THE INVENTION

In orthodontic practice, forces are applied over time to malaligned teeth in order to gradually adjust their orientation as desired. Although numerous techniques are used for generating the necessary forces and applying them to the teeth, the most common system in use today includes an orthodontic archwire spanning the affected teeth, and cooperating orthodontic brackets mounted to the teeth which include one or more slots for receiving the archwire. The brackets typically include tie wings which are used to ligate an archwire into a receiving slot, generally by means of small elastic O-rings, other elastic ligatures, or orthodontic ligating wire.

To achieve ideal positioning of a malaligned tooth, it may be necessary to adjust the tooth elevation (up-down location within the socket), rotation (about the apical axis), tilt or tip (mesial or distal angular adjustment), and torque (lingually or facially). Where necessary, a combination of these adjustments may be made simultaneously by applying the appropriate forces to the tooth through the orthodontic bracket and, in some instances, additional appliances.

One of the simplest bracket types in widespread use today is the so-called "single" bracket, such as the Alexander "Mini Brackets" distributed by ClassOne® Orthodontics. Single brackets include a base for mounting to the tooth, typically by directly cementing the base to the enamel surface of the tooth. Alternatively, the base may be secured to a metal band which encircles the tooth in some applications. The single bracket includes a facially oriented slot for receiving the archwire, which is located in the center portion of present brackets. The slot may be dimensioned and angled to generate, in combination with the archwire, desired forces for transmission to the tooth. To secure the archwire in the slot, the single bracket typically includes a pair of opposed tie wings for securing an elastic or other type of ligature.

The size of a standard single bracket has been determined by a number of factors relating to its orthodontic performance, its necessary strength to resist forces acting against portions of the bracket, and the necessity for adhering the device securely to the tooth. With regard to orthodontic performance, in order to accomplish certain realignments (e.g. rotation) additional elements, such as contacting arms, are typically added which increase the physical size of the bracket. To allow the bracket to transmit the forces generated by these elements to the tooth, a substantial contact area and base size have been required, including a significant mesiodistal width. With regard to strength and attachment to the tooth, one of the principal factors determining the size of present brackets is the need to reliably resist the large external forces which periodically act against the bracket. Significant among these are the forces generated when biting and chewing, particularly the occlusal forces acting against brackets adhered to the incisors and bicuspids when biting through or chewing certain foods. These forces also tend to break the tie wings or tie wing supports, resulting in failure of the bracket.

To overcome these problems, single brackets typically have a robust size so that the tie wings and their supports are sufficiently strong to resist these forces. In turn, the base and contact area with the tooth must be relatively large to resist the dislodging occlusal forces generated by food acting against the substantial occlusal face of the bracket. Single brackets in present use are typically 3–3.5 millimeters in length on the apical axis, and 2.5 millimeters or more in mesiodistal width. The base areas of such brackets are typically 7 square millimeters and greater.

Another bracket type in widespread use is the so-called "twin" or "double" bracket, exemplified by the Alexander Mini Bracket twin distributed by ClassOne® Orthodontics, or the Unitek Miniature Twin bracket by 3M®. It includes two structures for cooperating with an archwire, each having a facially opening slot in the center portion and a pair of tie wings. Because the overall bracket is typically larger than a single bracket, sufficient base surface is provided to reliably mount the bracket against the occlusal dislodging forces encountered due to the substantial occlusal face of the device, and to transmit the desired alignment forces to the tooth.

Although techniques have been perfected which can accomplish the desired orthodontic realignments, there remain several shortcomings with the presently known systems. Of significant importance, the aesthetics of present systems continues to present a substantial impediment to more widespread acceptance. As noted, single and double brackets, even those promoted as "mini" or "miniature," are relatively large in comparison to the front surfaces of the teeth, particularly the narrow incisors and short crown bicuspids. Yet these are the teeth most noticeable when one smiles, making present brackets highly noticeable in use. Brackets have typically been manufactured from stainless steel or similar metals because of their substantial strength, ease of fabrication and relative biological inertness. Unfortunately, metals result in a bracket which is generally considered to be unsightly, and therefore there is substantial patient resistance to the present metal brackets.

Present brackets also result in undesirable adverse effects on the gingiva. Because of their substantial occlusal faces, they interfere with a substantial portion of the food passing over or near to the tooth surface when biting or chewing, preventing food from contacting portions of the gingiva. This deprives the affected gingiva of normal and desirable massaging, and can result in gingival deterioration. Large brackets also tend to collect and hold more food particles, which can exacerbate problems and lead to gingivitis. Further, although stainless steel is an excellent material for bracket construction, certain individuals exhibit allergic sensitivity to nickel, which is part of typical stainless alloys. These problems are exacerbated by the large quantity of stainless steel in close proximity to the gingiva required by present brackets, and may result in some cases in hypertrophic gingiva or fibrotic tissue growth.

In response to these problems, numerous orthodontic systems have been developed which include transparent (e.g. crystalline alumina), ceramic, or other tooth-colored or transparent materials. The intent of these brackets is to minimize the aesthetic impact of the bracket. Unfortunately, these alternative materials have mechanical disadvantages compared to stainless steel. Thus a non-metallic bracket having adequate physical strength to resist fracture must typically be correspondingly larger, and therefore more noticeable. This is particularly true where the bracket must accomplish a rotational realignment, and therefore must include additional structures to generate the desired rotation force. Brackets made from alternative materials also tend to be more expensive than metal brackets. Such unfortunate trade-offs continue to frustrate those interested in effective but aesthetically acceptable orthodontics.

Where additional rotation force is required in conjunction with existing brackets, it is known to utilize rotation wedges having an elastomeric body which is secured between the archwire and the tooth surface, next to a bracket. The force generated by the partially compressed body of the wedge supplements forces which may be generated by the bracket itself. One common type of rotation wedge includes a thin web having two apertures which may be passed over one of the pairs of tie wings on a double bracket. These are typically used only in connection with double brackets, since the web occupies one set of the wings and therefore requires another pair of tie wings to ligate an archwire. Alternatively, it is known to provide two relatively large ligating loops as part of the elastomeric wedge in combination with a particular bracket design, where the loops may be "crisscrossed" under and over the tie wings, to both secure the wedge in position and ligate an archwire. There are several shortcomings with these known devices. Those which require a separate pair of tie wings, and therefore use of a double bracket, result in an orthodontic appliance which is aesthetically displeasing, particularly for use on the incisors or bicuspids. The double ligations of the "crisscross" wedge also present an unsightly appearance. Further, the body portions of known devices have relatively large and flat occlusal surfaces which may generate substantial forces when contacted by food during biting or chewing. These forces are ultimately transmitted to the bracket, either directly or through the archwire, and can therefore tend to dislodge the bracket.

Accordingly, a need exists for an orthodontic system which can provide the necessary corrective forces for adjusting malaligned teeth in conjunction with an archwire, which is aesthetically acceptable to a larger number of users. In particular, there remains a need for an orthodontic bracket which minimizes the aesthetic problems associated with such devices. Simultaneously, there is a need for such a bracket which can resist fracturing or occlusal dislodging forces as part of a secure and affordable orthodontic system. There is also a need for a bracket and system which minimizes or eliminates adverse gingival effects, by permitting more normal massaging when biting, and by significantly reducing the volume of metallic alloys required. Where additional rotation forces are required, there is a further need for an orthodontic system including a rotation wedge which can simultaneously ligate an archwire to a single bracket, including a miniature bracket, while providing necessary rotational force and minimizing any additional dislodging forces acting on the bracket.

SUMMARY OF THE INVENTION

To achieve these desired goals, the present invention includes an orthodontic bracket which is substantially smaller than any previous archwire ligating bracket. In particular, in a preferred embodiment a bracket is provided which has a base and means for cooperating with an archwire, wherein the base has a mounting surface of substantially 6 square millimeters or less, or in particularly preferred embodiments, substantially five square millimeters or less.

In an important aspect of the invention, an orthodontic bracket is provided which has an elongated configuration that, among other benefits, minimizes occlusal dislodging forces. For example, the bracket (including base) may preferably have a mesiodistal width of less than or equal to substantially two millimeters, or in particularly preferred embodiment, 1.5 millimeters. In relative dimensions, the present bracket may have an apical length which is equal to or greater than substantially 2 times the mesiodistal width, and in particularly preferred embodiments, 2.5 times the mesiodistal width. It has been found surprisingly that this small size, in combination with the novel slender aspect ratio of the bracket, provides a stable bracket which simultaneously reduces dramatically the negative aesthetic impact of the device, while reducing the occlusal dislodging forces generated by biting and chewing. In fact, these forces are reduced so significantly that the bracket remains securely attached, despite its small size and correspondingly tiny base (cemented) area, contrary to conventional expectation.

To further reduce occlusal dislodging forces and permit a small profile bracket which is suitably stable, the present invention may also include a base having an extended occlusal end, which in preferred embodiments will extend beyond the occlusal limit of any means for cooperating with an archwire for substantially one sixth the total apical length of the base or more. The occlusal end of the base may be tapered in the occlusal direction to a point having no extended surface substantially perpendicular to the apical axis. In particular, the occlusal end may include a mesiodistal taper, or both a mesiodistal and lingual taper, in the occlusal direction. Preferably the taper extends over only approximately the occlusal one half to one third of the apical length of the bracket, while substantially the gingival one half of the apical length of the bracket has a substantially constant mesiodistal width. The taper may affect one or both side(s) of the appliance, and the tapered side(s) will form an acute angle with respect to each other. In preferred embodiments the sides form angles with respect to the apical axis of less than or equal to substantially 45 degrees, and preferably less than or equal to substantially 30 degrees. Similarly, in a preferred embodiment the occlusal tie wing is tapered, and the gingival tie wing is not.

This configuration provides a bracket having sufficient strength for securely attaching to a tooth surface and transmitting desired orthodontic forces to the tooth when ligated to an archwire, while simultaneously minimizing the occlusal dislodging forces acting against the bracket under certain circumstances. Where present, the acutely tapered and/or pointed occlusal portion aids in deflecting food to minimize forces, while the non-tapered gingival portion provides necessary strength to the bracket while passing the deflected food along its substantially straight sides with minimum additional dislodging forces.

In particularly preferred embodiments, a sloped raised portion is included on the occlusal end or, where present, extension of the base. During biting, this raised portion will contact food passing along or near the front surface of the tooth before the food contacts the remaining portions of the bracket. In this manner the highly tapered base, alone or in conjunction with a tapered raised portion, will split or deflect the food before it contacts the remaining structures (e.g. the occlusal tie wing), thereby reducing any dislodging forces acting against the bracket. This deflection may be aided by providing a tapered occlusal/facial surface for the raised portion or wedge which is substantially aligned with the facial surface of the occlusal tie wing, so that deflected food will be directed to pass substantially over the tie wing with minimum interference or dislodging force.

In another aspect of the invention, the occlusal and gingival members for cooperating with an archwire are designed to provide an archwire slot which opens facially and is in the gingival one half of the bracket, rather than substantially centered as presently known. This novel orientation increases relatively the length of the occlusal portion of the bracket which, in combination with previously described features, further reduces the dislodging forces acting against the bracket. In addition, the bracket having this novel archwire slot orientation can be mounted more gingivaly on the tooth without interfering with the gingiva or requiring removal of gingiva, which is often required today. On those teeth having short crowns (e.g. bicuspids) the gingival slot orientation permits the centroid (center of rotation) of the bracket to be closer to the desired location on the tooth, improving the orthodontic performance of the system. A shorter profile bracket which nevertheless meets necessary strength and design constraints is also possible with the gingival slot orientation.

The resulting miniature bracket is preferably cast or otherwise formed from stainless steel or other noble metals, to take advantage of their preferable strength and durability characteristics. Since the features of the invention permit a substantially smaller bracket than previously known, the aesthetic and allergic disadvantages of stainless steel are minimized or eliminated. The resulting orthodontic system has been found to be less objectionable than present ceramic or transparent systems, and substantially less objectional than present metallic systems.

To provide necessary rotation forces, a rotation wedge may be used in conjunction with the above-described bracket as part of an orthodontic system. A particularly preferred rotation wedge includes an elastic body and an integral ligating web. The ligating web includes an aperture proximate the elastic body through which the archwire is passed, so that the elastic body will reside between the archwire and the tooth surface next to the bracket in use. Two tie wing apertures are provided outboard of the archwire aperture. In use, the elastic web surrounding these tie wing apertures is distended to pass respectively over the gingival and occlusal tie wings, so that the apical outermost portions of the web surrounding these apertures is secured behind the tie wings. The distance between the tie wing apertures is selected so that when the web is secured behind the tie wings as described above, that portion of the web between the apertures will pass over the facial surface of the archwire and securely ligate the archwire to the bracket in the slot. In other embodiments, a single aperture is provided for cooperating with both of the tie wings. Thus, a single element provides desired rotation force through the elastic member, while simultaneously mounting the elastic member in the desired position next to the bracket, and simultaneously providing simple and aesthetically pleasing ligation of the archwire to the bracket.

As further features of the present invention, the portion of the rotation wedge body which is occlusal to the archwire may preferably be tapered toward the tooth surface (lingually) in the occlusal direction. If desired, a mesiodistal taper may also be provided. In this manner, food which contacts the occlusal surface of the rotation wedge during biting or chewing will be more gradually deflected, thereby minimizing any dislodging forces generated by the wedge and transmitted to the bracket. Tapers may also be provided on the gingival portion of the rotation wedge for aesthetic purposes, to maximize comfort, and/or to provide a wedge which may be used in any orientation.

Finally, to further reduce any potential dislodging forces when the rotation wedge and bracket of the present invention are used in combination in an orthodontic system, the web portion of the wedge may include an extension below the occlusal tie wing aperture having a width approximately equal to the corresponding width of the associated bracket. The occlusal end of this extension may be angled or otherwise configured so that when the web is in place behind the tie wing of the bracket, the extension will substantially fill any remaining space between the bracket base and the tie wing. In this manner, a substantially continuous occlusal/facial surface is presented, and food which is initially deflected by the bracket base or raised portion will continue to be deflected by the surface of the web extension, and ultimately by the facial surface of the occlusal tie wing. If desired, similar extensions may be provided outboard of each of the tie wing apertures.

BRIEF DESCRIPTION OF THE DRAWINGS

FIG. 1 is a perspective view of a typical prior art double bracket.

FIG. 2 is a perspective view of a typical prior art single bracket, including rotational force arms.

FIG. 3A is a perspective view of one embodiment of an orthodontic bracket according to the present invention.

FIG. 3B is a perspective view of another embodiment of an orthodontic bracket according to the present invention.

FIG. 4 is a side view of one embodiment of an orthodontic bracket according to the present invention.

FIG. 5 is a front view of the orthodontic bracket of FIG. 4.

FIG. 6 is a side view of another embodiment of an orthodontic bracket according to the present invention.

FIG. 7 is a side view of a preferred embodiment of an orthodontic bracket according to the present invention.

FIG. 8 is a front view of the orthodontic bracket of FIG. 7.

FIG. 9 is a front view of one embodiment of a rotation device according to the present invention.

FIG. 10 is a cut-away view of a portion (A—A) of the rotation device of FIG. 9.

FIG. 11 is an enlarged cut-away view of another portion (B—B) of the rotation device of FIG. 8, including a phantom representation of a portion of an orthodontic bracket.

DETAILED DESCRIPTION OF THE PREFERRED EMBODIMENTS

Figure 12:
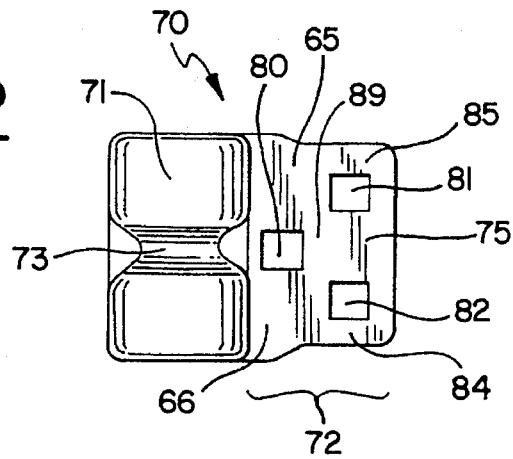
FIG. 12 is a front view of another embodiment of a rotation device according to the present invention.

FIGS. 1 and 2 illustrate representative prior art orthodontic brackets. In particular, FIG. 1 shows a double bracket which includes a base 11 and twin elements 12, 13 for cooperating with an archwire. Each of the archwire elements includes a slot 16 for receiving an archwire, and occlusal and gingival tie wings 14, 15 (respectively) for cooperating with ligating bands or wire to secure the archwire in slot 16. It should be understood that "occlusal" as used herein and in the attached claims, refers generally to the non-gingival (i.e. incisal or occlusal) direction. As illustrated, the standard double bracket has a considerable mesiodistal width, and thus a pronounced appearance on the tooth surface in use. As shown in FIG. 1, it is known to provide the occlusal side of base 11 with angled surfaces forming an obtuse angle to one another and angles of greater than 45 degrees to the apical axis, and intersecting at a terminus 17.

FIG. 2 shows a comparative example of a typical prior art single bracket. Similar to the double bracket, the single bracket includes a base 21 which has substantial mesiodistal and apical dimensions. It is known to provide the occlusal end of the base with a curved surface, or with tapered sides forming an obtuse angle. Mounted to the facial surface of the base is a single means for cooperating with an archwire, including tie wings 24, 25 and archwire slot 26. The archwire slot is substantially in the center portion of the bracket relative to the apical axis. As illustrated, the tie wings of a single bracket typically have substantial mesiodistal width in order to provide adequate mechanical strength and, in particular, to resist occlusal forces during biting.

Also illustrated in FIG. 2 are representative appliances which are commonly included with prior art single brackets to accomplish desired tooth rotation. In particular, rotating wings 28 attached to the base 21 are provided, which angle away from the base and toward the back of the archwire. The front edge 29 of the wings 28 is intended to contact the back surface of the archwire and thereby transmit a rotation force to one side of the bracket when an archwire is ligated in slot 26. Known single brackets suffer from the same problem as the prior art double bracket, namely substantial mesiodistal width and bulk is required in order to provide the desired realigning forces and to resist occlusal dislodging forces and breakage.

In comparison, FIG. 3A (and also FIGS. 4 and 5) illustrates one embodiment of the present orthodontic bracket 10 for use in the present system. As shown, bracket 10 includes a base 31 for mounting the appliance to a tooth. The appliance is preferably cemented directly to the enamel surface of the tooth, and the back (or lingual) surface of base 31 may include means for increasing its adhesive bond to the tooth such as grooves, recesses or other surface-extending features. Alternatively, the bracket 10 could be secured to other mounting structures, such as bands, although the aesthetic impact of such mounting structures is less desirable.

A means for cooperating with an archwire is attached to the facial surface of the base 31. It will be understood in conjunction with the present description and claims that "attached" is intended to include structures which are formed separately but joined in use, as well as integral structures formed of a single, continuous medium. The archwire cooperating means illustrated includes a gingival tie wing 35, an occlusal tie wing 34, and an archwire slot 36 formed between the tie wings 34, 35 and their respective bases. Other means for cooperating with an archwire which are known to those skilled in this art may alternatively be utilized.

Additional details of a preferred embodiment can best be understood in connection with FIGS. 4 and 5. The base 31 includes a gingival half 41 and an occlusal half 42. In the embodiment illustrated, substantially the gingival half of base 31 has a substantially constant mesiodistal width, while at least a portion of the occlusal half is tapered in the occlusal direction. Preferably, the taper extends over at least substantially the occlusal one third or one half of base 31. The mesial and distal edges of the base in the tapered region join at an occlusal point 38 and form an acute angle with respect to each other, in contrast to the obtuse angles previously known. These features of the base will assist in splitting and/or deflecting food around the bracket as the tooth and bracket are moved through a food substance during biting or chewing. This, in turn, significantly reduces the resulting forces acting against the bracket, so that the comparatively tiny base area presented by the preferred embodiments can nevertheless provide a particularly secure attachment to the tooth surface.

To further minimize occlusal dislodging forces during biting, the remaining elements of the occlusal one half of the bracket 10 may be similarly tapered. For example, in the preferred embodiment occlusal tie wing 34 is tapered in the occlusal direction similar to the occlusal portion of base 31. In contrast, gingival tie wing 35 has a substantially constant mesiodistal width. This also minimizes occlusal dislodging forces, since food may pass smoothly along the substantially parallel sides of the gingival portion of the bracket, including gingival tie wing 35, without generating any significant additional forces. This is in contrast to prior devices, which if tapered at all, have typically been tapered over the entire apical length of the appliance.

The tie wings 34, 35 include overhanging portions which define recesses 44, 45 for receiving ligating means. These will typically include elastomeric rings, rubber bands, strings, clips, or ligating wire, although other ligations or structures may be used without departing from the scope of the invention.

An archwire slot 36 is shown between the tie wings 34, 35, and formed in part (surfaces 51, 52) by the inner surfaces of the tie wings and the tie wing support bases. The bottom surface 50 of the archwire slot 56 is formed by a portion of the bracket body 46 or base 31. Ideally, portion 46 of the body (when present) is as thin as possible so that the archwire will lie close to the tooth surface, thereby further minimizing any dislodging forces or moment imparted against the bracket/tooth bond. However, in an alternative embodiment, the thickness of body portion 46 may be selected or adjusted to e.g. accommodate a desired archwire curve, or to provide desired orthodontic forces to the tooth.

In general, the width, depth, and angular orientation in all axes of the archwire slot may be selected to accommodate the particular tooth orientation and orthodontic forces which are required. In a preferred embodiment for use with 0.018 inch archwire, the archwire slot 36 is 0.018 inches wide (apical) and approximately 0.025 inches deep. It will further be understood that other means for cooperating with an archwire (such as buccal tubes, tunnels, and other structures), as well as optional means for providing desired orthodontic forces (such as lever arms, springs, spring or ligation mounts, clips, etc.) may similarly be provided in conjunction with the present system, including bracket 10, without departing from the scope of the present invention.

The overall dimensions of bracket 10 may similarly depend upon the specific orthodontic application at issue. However, the unique slender design and narrow aspect ratio of the bracket base and/or body are important aspects of certain embodiments of the invention. In preferred embodiments, the mounting surface of the base 31 has a total surface area of substantially 6 square millimeters or less, and in particularly preferred embodiments, substantially 5 square millimeters or less which is a fraction of the base area of known slotted ligating brackets. To achieve the slim design desired, it is preferable for the bracket to have an overall mesiodistal width of substantially 2 millimeters or less, or in particularly preferred embodiments, 1.5 millimeters or less. In relative dimensions, it is preferable for the bracket to have apical length which is equal to or greater than substantially 2 times the mesiodistal width, and in particularly preferred embodiments, equal to or greater than 2.5 times the mesiodistal width. These embodiments may, or may not, further incorporate other aspects of the present invention, such as occlusal base extensions, tapers or wedges. In a preferred example, the base 31 has an apical length of approximately 3.75 millimeters, and a mesiodistal width in the gingival portion of approximately 1.2–1.5 millimeters.

In the preferred embodiments shown, the occlusal portion of the base (and preferably of the bracket) is tapered in the occlusal direction and intersect at an occlusal point. In particular, the mesial and distal sides of the bracket form an acute angle (although the sides may not be exactly linear), preferably with both sides angled with respect to the apical axis of the bracket 10. In preferred embodiments, the angle of the taper with respect to the apical axis is less than or equal to substantially 45 degrees, and in particularly preferred embodiments both sides of the occlusal portion are angled at substantially 30 degrees or less with respect to the apical axis.

The occlusal end 42 of base 31 tapers to a point 38, which may be rounded but has no substantial surface which is perpendicular to the apical axis. It is preferred that the base (and body) be tapered not only mesiodistally, but also in the lingual direction.

In other preferred embodiments, a raised portion 39 is provided, which may be on an occlusal extension of base 31. The raised portion 39 has a top 55 which is higher in the facial direction than the average thickness of base 31, so that it is attached to but generally rises above the base. As illustrated, the occlusal/facial edge 53 of portion 39 is preferably tapered from the top 55 toward occlusal point 38 of the base. It may also be tapered in the mesiodistal direction as illustrated, to provide a "wedge" for initially contacting and splitting food passing along or near to the surface of the tooth when biting. The gingival surface 54 of portion 39 may, if desired, be tapered toward the base to provide an increased recess 44 for receiving ligatures. In particularly preferred embodiments, occlusal or facial surface 53 of portion 39 is substantially aligned with facial surface 56 of occlusal tie wing 34 so that contacted food will ideally be deflected at an angle substantially coinciding with the surface of the occlusal tie wing so that food is deflected over the wing to minimize subsequent forces generated by contact between the food and the tie wings.

Although the deflecting raised portion on the occlusal base is discussed herein in connection with the preferred bracket 10, it should be understood that one or more such structures may also be provided in conjunction with existing bracket designs to aid with splitting and deflecting food. Where a bracket has sufficient width, such as a wide single or a double, two or more such features may be used (e.g. respectively occlusal to each set of tie wings) as shown in FIG. 3B.

FIG. 6, which illustrates another embodiment of bracket 10, does not include a raised portion 39. Instead, base 31 includes an occlusal extension at end 42 which extends beyond the occlusal point or limit of tie wing 34. This occlusal extension is acutely tapered in at least the mesiodistal direction as previously discussed, and preferably also tapered in the lingual direction.

FIGS. 7 and 8 illustrate a particularly preferred embodiment similar to that illustrated in FIGS. 3–5, but wherein the archwire slot 36, and in particular the bottom surface 50, is not substantially centered in apical direction but instead is uniquely located in the gingival one half of the bracket. In this configuration, the portion of the bracket incisal of the archwire is relatively longer than the gingival portion. The archwire is thus closer to the gingival edge of the bracket 10, including base 31. This is particularly advantageous for use on teeth having short crowns (such as bicuspids) where standard brackets often contact, or in some cases require removal of, gingival tissue in order to obtain the desired orientation of the archwire and to accommodate the base of the bracket. Further, the archwire will be at a correct level, or an improved level, for imparting certain corrective forces to the tooth. In particular, the centroid (center of rotation) of the bracket is placed in a beneficial and preferred position, in comparison to existing devices. In combination with these advantages, the relatively extended occlusal portion of the bracket provides the necessary mounting surface for mechanical attachment to the tooth, while, as previously mentioned, minimizing any dislodging forces. By locating the slot 36 in the gingival one half, the overall facial height of bracket 10 may if desired be further reduced. Finally, the bracket retains its overall miniature size in comparison to existing devices, thereby enhancing its aesthetic acceptance.

Although there are many advantages of a single bracket, and in particular numerous distinct advantages of the inventive miniature single bracket described above, it may be difficult to generate or transmit sufficient rotational force to accomplish some desired orthodontic realignments. Accordingly, the present orthodontic system may further include a rotation wedge particularly adapted for beneficial use in conjunction with the orthodontic bracket previously described.

Figure 13:
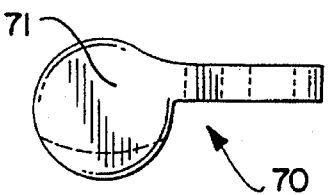
FIG. 13 is a top view of the rotation device of FIG. 12.

Referring first to FIGS. 12 and 13, they show a basic embodiment of rotation wedge 70. It includes an elastic body 71 which may have any cross-section desired, but is illustrated as generally cylindrical. Body 71 may include means for assisting with the orientation of the device, such as groove 73 for cooperating with an archwire. Other similar means may alternatively be used if desired.

Contiguous with body 71 is a thin web portion 72 having in some instances three apertures. The first, archwire aperture 80, is centered in the apical direction relative to body 71 and is proximate to body 71. Archwire aperture 80 is dimensioned to receive the archwire, which is passed through aperture 80 with body 71 on the inside or lingual side of the archwire.

The second and third apertures, tie wing apertures 81 and 82, are located near the opposite end of web 72 away from body 71. Center portion 75 of the web is the portion between apertures 81, 82 and is aligned on the mesiodistal axis with archwire aperture 80 and, if present, archwire slot 73. The apical peripheral portions 84, 85 of the web form ties which will, in use, reside beneath the tie wings of a bracket, such as in recesses 44, 45 of bracket 10. Apertures 80, 81 and 82 are preferably rectangular, although other shapes may be used without departing from the scope of the present invention.

Figure 14:
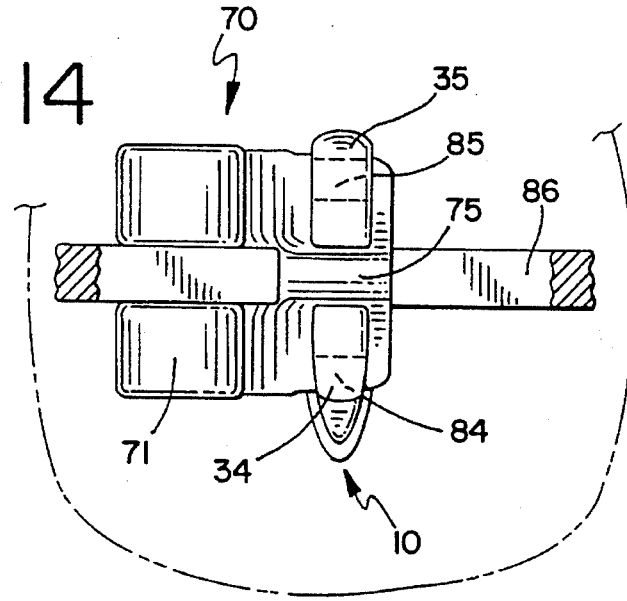
FIG. 14 is a front view of an orthodontic system according to the present invention, including an embodiment of a rotation device in combination with an embodiment of an orthodontic bracket.
Figure 15:
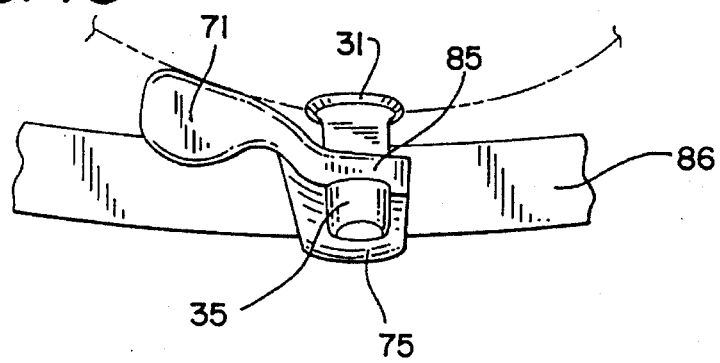
FIG. 15 is a top view corresponding to FIG. 14.
Figure 16:
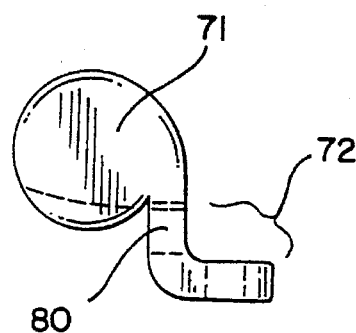
FIG. 16 is a top view of another embodiment of a rotation device according to the present invention.
Figure 17:
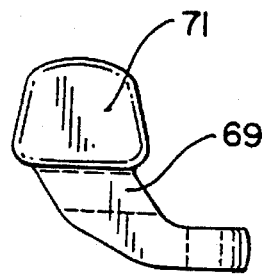
FIG. 17 is a top view of another embodiment of a rotation device according to the present invention.

The sides of the apertures may all be perpendicular to the face of web 72, although it may be preferred to angle archwire slot 80 to accommodate the archwire in use. Similarly, one or more bends may be provided in the mesiodistal profile of web 72, and preferably two forming an "L" or "Z" profile (e.g. FIG. 16), to better accommodate the distortion of a flat web 72 in use as shown in FIGS. 14 and 15. As shown in the example of FIG. 17, in some embodiments the web portion may be contiguous with the facial surface of body 71, such that aperture 69 may define a tunnel through a portion of the web and/or body 71. In such embodiments, a groove 73 or other additional means for positioning body 71 will generally not be required.

FIGS. 14 and 15 show a rotation wedge 70 in combination with bracket 10 and archwire 86. In preparation for assembly of the orthodontic system including these elements, the desired wedge (or wedges) 70 is threaded onto the archwire 86 as previously mentioned. As the archwire is moved into position, the wedge is located proximate to the bracket on the tooth whose rotation is to be influenced. The archwire is then inserted into the brackets in manners known in the art, and may be secured generally in place with one or more ligatures on other brackets.

The body 71 of the wedge is positioned between the tooth surface and the archwire. To secure the wedge in this location while simultaneously ligating archwire 86 to the associated bracket 10, the tie wing apertures 81, 82 are sequentially passed over the respective tie wings so that the apertures encircle the corresponding tie wings and/or support bases, with portions 84, 85 residing beneath the corresponding tie wings 34, 35. The width of web portion 75, and thus the distance between tie wing apertures 81, 82, is selected to correspond with the separation of the tie wings and to provide the desired ligating force to web portion 75 (which remains on top of archwire 86 and therefore secures it in slot 36).

Figure 18:
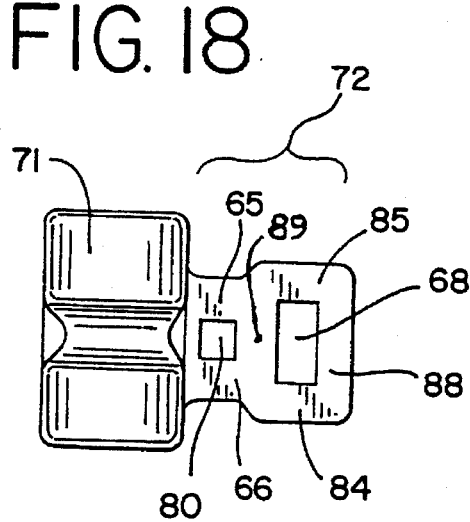
FIG. 18 is a front view of another embodiment of a rotation device according to the present invention.
Figure 19:
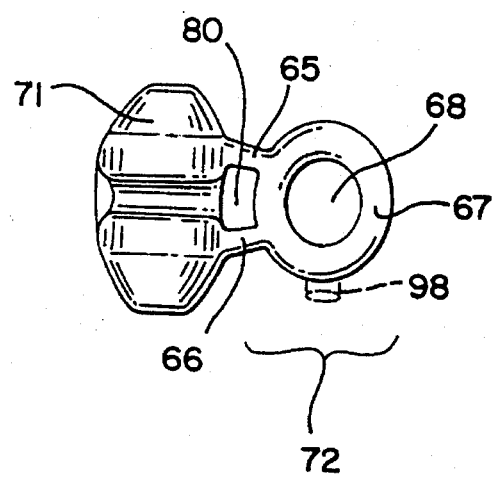
FIG. 19 is a front view of another embodiment of a rotation device according to the present invention.
Figure 20:
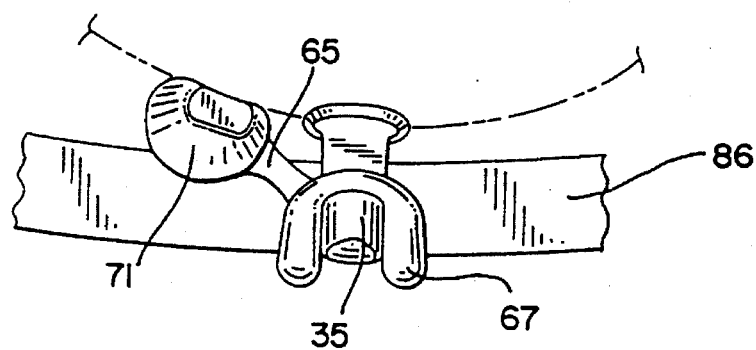
FIG. 20 is a top view corresponding to FIG. 19.

In an alternative embodiment as shown in FIG. 18, web portion 75 may be eliminated so that a single ligating aperture 68 is provided. In such cases, the portions of the web 88, 89 which are mesial and distal to the ligating aperture pass over the facial surface of archwire 86 and ligate it to bracket 10, as shown in FIG. 20. The cross-sectional area of portions 88, 89, as well as 84, 85, may be selected to provide the desired ligating force, and may differ from other areas of the web. If desired, the resulting web may have a rounded or circular design, such as that of a standard O-ring shaped ligature 67 (FIGS. 19, 20) with connections 65, 66 to body 71 defining an archwire aperture. Extensions 98 may be included on ligature 67 if desired. The portions of the web above and below aperture 80 may be dimensioned to minimize their visibility (such as by reducing their apical width as in FIG. 18), while still functioning to retain body 71 in position.

The body 71 and web 72 are preferably molded from any suitable elastomeric materials known in the art. The particular dimensions of the apertures and web will depend upon the corresponding dimensions of the associated bracket, and the ligating force which is desired. The rotational force generated by the wedge 70 may be controlled by selecting the diameter and/or resiliency of body 71; the thickness of groove 73 (if used); the shape of body 71; or the relative location of body 71 with respect to the tooth surface (such as by adjusting the length of the web to provide greater or lesser offset to body portion 71). It is anticipated that the preferable method for adjusting the amount of rotation will be by selecting a wedge 70 from a collection including wedges having body portions 71 with differing dimensions to impart different forces to a tooth.

FIGS. 9, 10 and 11 illustrate various aspects of alternative embodiments of rotation wedge 70. To minimize dislodging forces generated by food contacting body 71 of wedge 70, which may in part be transmitted to bracket 10 either directly or through archwire 86, it is desirable to provide an angled tapered surface 91 on the occlusal portion of body 71. As shown in FIG. 9, the angled surface 91 tapers lingually toward the tooth surface. If desired, body 71 may also have a mesiodistal taper 92 in the occlusal direction, on either one or both sides of the body 71. In particular embodiments, tapers (such as tapers 93–95) may be provided on the opposite end of body 71 as well. Such tapers may enhance the aesthetic appearance of the rotation wedge in use, and may enhance comfort. In addition, where the wedge 70 is substantially symmetrical about the mesiodistal center line, it may be installed on either the mesial or distal sides of the tooth to induce the desired clockwise or counterclockwise rotation, as required. Where the device is non-symmetrical, mirror image wedges may be used for the alternative rotations.

As shown in FIG. 9, when archwire slot 36 is located in the gingival half of the corresponding bracket, the rotation wedge may similarly have an extended occlusal portion, shown by the dotted line 96. In this configuration, a more acute angle can be provided for the tapered surface 91, further reducing the dislodging forces which are generated.

Finally, web 72 may be provided with an extension 90 extending away from the web in apical alignment with the tie wing apertures 81, 82. As previously mentioned, portion 84 of web 72 resides beneath the tie wing of a bracket in use, such as within recess 44 of bracket 10. Where the cross-sectional area of web portion 84 is less than the cross-sectional area of recess 44, the bracket/rotation wedge combination will include a notch at the entrance of recess 44 which could undesirably engage or accumulate food during biting. Accordingly, an extension or enlarged area 90 may be provided on the web so that, in conjunction with portion 84, the corresponding bracket recess is substantially filled, as shown in FIG. 10. The occlusal or facial surface 97 of extension 90 may be configured to provide a surface which is substantially co-extensive with the upper surface 56 of tie wing 34 and, if present, the occlusal or facial surface 53 of raised portion 39. In this manner, the bracket/rotation wedge combination presents a substantially continuous tapered occlusal/facial surface so that food which contacts the occlusal point 38 or surface 53 and is deflected, will be urged smoothly across the entire facial surface of the device without intruding into recess 44 or catching on the occlusal end of tie wing 34. Alternatively, the cross-section of portion 84 of the web may be selected to provide the desired functions discussed above. If desired, a second extension 98 may be provided on the opposite side of web 72, so that wedge 70 may be used in either orientation. The gingival extension (relative to orientation in use) may be cut off before installation of the device if desired.

Although the preferred material for bracket 10 is stainless steel, other materials having suitable strength and biological inertness could similarly be used, and the present invention is not limited to any particular material. Finally, although the devices are illustrated in conjunction with a single rectangular archwire, the present invention is not limited thereto but may encompass other orthodontic techniques as well, such as multiple wire or round wire orthodontics.

It shall be understood that the present invention, including the orthodontic bracket, the rotation wedge, and the orthodontic system, may be embodied in other specific forms without departing from the spirit or essential characteristics of the present invention. The present embodiments are, therefore, to be considered in all respects as illustrative only and not as restrictive. All changes which come within the meaning and range of the equivalence of the claims are, therefore, intended to be embraced therein.

I claim:

1. An orthodontic archwire bracket comprising:
   a base having an occlusal end and a gingival end on the apical axis, said base having a facial surface and a mounting surface;
   means for cooperating with an archwire, said means attached to said facial surface of said base;
   said bracket having an apical length which is equal to or greater than substantially 2 times the average mesiodistal width of said bracket.

2. The orthodontic bracket of claim 1 wherein the apical length of said bracket is equal to or greater than substantially 2.5 times the average mesiodistal width of said bracket.

3. The orthodontic bracket of claim 1 wherein the average mesiodistal width of said bracket is equal to or less than substantially 2 millimeters.

4. The orthodontic bracket of claim 1 wherein the average mesiodistal width of said bracket is equal to or less than substantially 1.5 millimeters.

5. The orthodontic bracket of claim 1 wherein said mounting surface of said base is adapted for mounting directly to a tooth surface.

6. The orthodontic bracket of claim 1 wherein said means for cooperating with an archwire comprises tie wings for ligating an archwire.

7. The orthodontic bracket of claim 1 wherein the apical length of said bracket is equal to or greater than substantially 3 times the average mesiodistal width of said bracket.

8. The orthodontic bracket of claim 1 wherein the average mesiodistal width of said bracket is equal to or less than substantially 1.2 millimeters.

9. An orthodontic archwire bracket comprising:
   a base having an occlusal end and a gingival end on the apical axis, said base having a facial surface and a mounting surface;
   means for cooperating with an archwire, said means attached to said facial surface of said base;
   said base having an apical length which is equal to or greater than substantially 2 times the average mesiodistal width of said base.

10. The orthodontic bracket of claim 9 wherein the apical length of said base is equal to or greater than substantially 2.5 times the average mesiodistal width of said base.

11. The orthodontic bracket of claim 9 wherein the average mesiodistal width of said base is equal to or less than substantially 2 millimeters.

12. The orthodontic bracket of claim 9 wherein the average mesiodistal width of said base is equal to or less than substantially 1.5 millimeters.

13. The orthodontic bracket of claim 9 wherein the apical length of said base is equal to or greater than substantially 3 times the average mesiodistal width of said base.

14. The orthodontic bracket of claim 9 wherein the average mesiodistal width of said base is equal to or less than substantially 1.2 millimeters.

15. An orthodontic archwire bracket comprising:
   a base having an occlusal end and a gingival end on the apical axis, said base having a facial surface and a mounting surface;
   means for cooperating with an archwire, said means attached to said facial surface of said base;
   said means for cooperating with an archwire having an apical length which is equal to or greater than substantially 2.5 times the maximum mesiodistal width of said means for cooperating with an archwire.

16. The orthodontic bracket of claim 15 wherein the apical length of said means for cooperating with an archwire is equal to or greater than substantially 3 times the maximum mesiodistal width of said means for cooperating with an archwire.

17. The orthodontic bracket of claim 15 wherein the maximum mesiodistal width of said means for cooperating with an archwire is equal to or less than substantially 2 millimeters.

18. The orthodontic bracket of claim 15 wherein the maximum mesiodistal width of said means for cooperating with an archwire is equal to or less than substantially 1.5 millimeters.

19. The orthodontic bracket of claim 15 wherein the maximum mesiodistal width of said means for cooperating with an archwire is equal to or less than substantially 1.2 millimeters.

20. An orthodontic archwire bracket comprising:
   a base having an occlusal end and a gingival end on the apical axis, said base having a facial surface and a mounting surface;
   means for cooperating with an archwire, said means attached to said facial surface of said base;
   said base having an apical length which is equal to or greater than substantially 1.5 times the maximum mesiodistal width of said base, and having a maximum mesiodistal width of substantially 2 millimeters or less.

21. The orthodontic bracket of claim 20 wherein said maximum mesiodistal width is substantially 1.5 millimeters or less.

22. The orthodontic bracket of claim 20 wherein said maximum mesiodistal width is substantially 1.2 millimeters or less.

23. An orthodontic bracket comprising:
   a base having an occlusal end and a gingival end on the apical axis, said base having a facial surface and a mounting surface;
   means for cooperating with an archwire, said means attached to said facial surface of said base;
   the apical length of said bracket being equal to or greater than substantially 2 times the maximum mesiodistal width of said bracket.

24. The orthodontic bracket of claim 23 wherein the apical length of said bracket is equal to or greater than substantially 2.5 times the maximum mesiodistal width of said bracket.

25. The orthodontic bracket of claim 23 wherein the maximum mesiodistal width of said bracket is equal to or less than substantially 2 millimeters.

26. The orthodontic bracket of claim 23 wherein the apical length of said bracket is equal to or greater than substantially 3 times the maximum mesiodistal width of said bracket.

27. The orthodontic bracket of claim 23 wherein the maximum mesiodistal width of said bracket is equal to or less than substantially 1.2 millimeters.

28. An orthodontic bracket comprising:
   a base having an occlusal end and a gingival end on the apical axis, said base having a facial surface and a mounting surface;
   a pair of tie wings attached to said facial surface of said base and defining an archwire slot, said tie wings adapted for ligating said archwire in said slot;
   said mounting surface adapted for attachment directly to a tooth surface and having an area of less than or equal to substantially 6.5 square millimeters.

29. The orthodontic bracket of claim 28 wherein said base has an apical length which is equal to or greater than substantially 2 times the average mesiodistal width of said base.

30. The orthodontic bracket of claim 28 wherein said mounting surface has an area of less than or equal to substantially 5 square millimeters.

31. The orthodontic bracket of claim 30 wherein said base has an apical length which is equal to or greater than substantially 2 times the average mesiodistal width of said base.

32. An orthodontic archwire bracket comprising:

a base having an occlusal end and a gingival end on the apical axis, said base having a facial surface and a mounting surface;

means for cooperating with an archwire, said means attached to said facial surface of said base;

said base having an apical length which is equal to or greater than substantially 2.5 times the average mesiodistal width of said base, said mounting surface having an area of less than or equal to substantially 5 square millimeters.

33. An orthodontic bracket comprising:

a base having an occlusal end and a gingival end on the apical axis;

means for cooperating with an archwire, said means attached to the facial surface of said base; and a raised portion on the facial surface at the occlusal end of said base, said raised portion including a occlusal side which is tapered in the occlusal direction.

34. The orthodontic bracket of claim 33 wherein at least the facial height of said occlusal side of said raised portion is tapered in the occlusal direction.

35. The orthodontic bracket of claim 34 wherein the thickness of said occlusal end of said base is also tapered in the occlusal direction.

36. The orthodontic bracket of claim 33 wherein at least the mesiodistal width of said occlusal side of said raised portion is tapered in the occlusal direction.

37. The orthodontic bracket of claim 36 wherein the mesiodistal width of said occlusal end of said base is also tapered in the occlusal direction.

38. The orthodontic bracket of claim 37 wherein said occlusal end of said base tapers to a point having no extended surface substantially perpendicular to the apical axis, and said raised portion is located proximate said point.

39. The orthodontic bracket of claim 33 wherein both the mesiodistal width and the facial height of said occlusal side of said raised portion are tapered in the occlusal direction.

40. The orthodontic bracket of claim 39 wherein both the thickness and the mesiodistal width of said occlusal end of said base are also tapered in the occlusal direction.

41. The orthodontic bracket of claim 33 wherein said bracket includes means for cooperating with an archwire, and wherein at least said occlusal side of said raised portion extends in an occlusal direction beyond the axial limit of said means for cooperating with an archwire, such that said tapered occlusal side of said raised portion will contact food when moved in an occlusal direction during biting before said archwire cooperating means.

42. The orthodontic bracket of claim 33 wherein the occlusal portion of said archwire cooperating means has a facial surface, and wherein the occlusal surface of said occlusal side of said raised portion is substantially aligned with said facial surface of said occlusal portion of said archwire cooperating means.

43. The orthodontic bracket of claim 42 wherein a ligature receiving recess passes between said raised portion and said archwire cooperating means.

44. The orthodontic bracket of claim 33 including two or more raised portions on said base.

45. The orthodontic bracket of claim 44 wherein said bracket comprises two or more individual means for cooperating with an archwire, and wherein said two or more raised portions are respectively aligned with said individual archwire cooperating means on the respective apical axes.

46. An orthodontic bracket comprising a base having an occlusal end and a gingival end, occlusal and gingival ligature retaining wings attached to the base, a slot between the occlusal and gingival wings for receiving an archwire, a raised portion at the occlusal tip of said base, and a ligature receiving recess between said raised portion and said occlusal ligature retaining wing, said bracket having an apical length which is equal to or greater than substantially 2 times the average mesiodistal width of said bracket.

47. An orthodontic bracket for use on the facial surface of a tooth comprising:

a base having an occlusal end and a gingival end on the apical axis, mesial and distal sides, a facial surface and a mounting surface;

means for cooperating with an archwire, said means attached to said facial surface of said base;

said base extending in the occlusal direction beyond the occlusal limit of said archwire cooperating means and having an apical length which is equal to or greater than substantially 2 times the mesiodistal width of said base.

48. The orthodontic bracket of claim 47 wherein said occlusal base extension is tapered in the occlusal direction.

49. An orthodontic bracket for use on the facial surface of a tooth comprising:

a base having an occlusal end and a gingival end on the apical axis, mesial and distal sides, a facial surface and a mounting surface;

means for cooperating with an archwire, said means attached to said facial surface of said base; and said base extending in the occlusal direction beyond the occlusal limit of said archwire cooperating means a distance equal to or greater than substantially one sixth the total apical length of said base, said bracket further comprising a raised portion on said occlusal base extension.

50. An orthodontic bracket for use on the facial surface of a tooth comprising:

a base having an occlusal end and a gingival end on the apical axis, mesial and distal sides, a facial surface and a mounting surface;

means for cooperating with an archwire, said means attached to said facial surface of said base; and said base extending in the occlusal direction beyond the occlusal limit of said archwire cooperating means a distance equal to or greater than substantially one sixth the total apical length of said base, said bracket further comprising a raised portion on said occlusal base extension.

51. An orthodontic bracket comprising:

an occlusal end and a gingival end on the apical axis, wherein the mesiodistal width of at least a portion of said occlusal end tapers in the occlusal direction to an occlusal intersection of the mesial and distal sides of said occlusal end;

a tapered raised portion defining a wedge located at said occlusal end;

said occlusal intersection having no extended surface substantially perpendicular to the apical axis and said sides of said occlusal end forming an acute angle.

52. The orthodontic bracket of claim 51 wherein both the mesiodistal width and the facial height of at least a portion of said occlusal end of said bracket taper in the occlusal direction.

53. The orthodontic bracket of claim 51 wherein the mesiodistal width tapers in the occlusal direction over at least substantially the occlusal one third of the apical axial length of said bracket.

54. The orthodontic bracket of claim 53 wherein the mesiodistal width of substantially the gingival one half of the apical axial length of said bracket is substantially constant.

55. An orthodontic bracket comprising:

an occlusal end and a gingival end on the apical axis, said occlusal end including mesial and distal occlusal sides;

said occlusal sides intersecting at an occlusal terminus, said terminus including a tapered raised portion defining a wedge, and said occlusal sides forming an acute angle with respect to one another.

56. The orthodontic bracket of claim 55 wherein said acute angle is less than or equal to substantially 60 degrees.

57. The orthodontic bracket of claim 56 wherein both of said mesial and distal occlusal sides are acutely angled with respect to the apical axis and form angles of less than or equal to substantially 30 degrees with respect to the apical axis.

58. The orthodontic bracket of claim 55 wherein both of said mesial and distal occlusal sides are acutely angled with respect to the apical axis.

59. An orthodontic bracket for use on the facial surface of a tooth comprising:

a base having an occlusal end and a gingival end on the apical axis, mesial and distal sides, a facial surface and a mounting surface;

means for cooperating with an archwire, said means attached to said facial surface of said base;

said base extending in the occlusal direction beyond the occlusal limit of said archwire cooperating means a distance equal to or greater than substantially one sixth the total apical length of said base; and a raised portion on said occlusal base extension.

60. An orthodontic bracket for use on the facial surface of a tooth comprising:

a base having an occlusal end and a gingival end on the apical axis, mesial and distal sides, a facial surface and a mounting surface;

means for cooperating with an archwire, said means attached to said facial surface of said base;

said base extending in the occlusal direction beyond the occlusal limit of said archwire cooperating means a distance equal to or greater than substantially one sixth the total apical length of said base, said occlusal base extension tapered in the occlusal direction; and a raised portion on said occlusal base extension.

* * * * *